(12) United States Patent
Olivares et al.

(10) Patent No.: US 6,793,790 B1
(45) Date of Patent: Sep. 21, 2004

(54) SAMPLE COLLECTION SYSTEM FOR GEL ELECTROPHORESIS

(75) Inventors: José A. Olivares, Los Alamos, NM (US); Peter C. Stark, Los Alamos, NM (US); John M. Dunbar, Santa Fe, NM (US); Karen K. Hill, Los Alamos, NM (US); Cheryl R. Kuske, Los Alamos, NM (US); Gustavo Roybal, Espanola, NM (US)

(73) Assignee: The Regents of the University of California, Oakland, CA (US)

( * ) Notice: Subject to any disclaimer, the term of this patent is extended or adjusted under 35 U.S.C. 154(b) by 303 days.

(21) Appl. No.: 09/875,333

(22) Filed: Jun. 6, 2001

(51) Int. Cl.[7] ..................... G01N 27/447; G01N 27/453
(52) U.S. Cl. ..................... 204/462; 204/461; 204/466; 204/612; 204/613; 204/616
(58) Field of Search ................ 204/456, 461, 204/462, 464, 466, 467, 606, 612, 613, 614, 616, 618

(56) References Cited

U.S. PATENT DOCUMENTS

| | | | |
|---|---|---|---|
| 3,791,950 A | * 2/1974 | Allington | 204/462 |
| 4,964,961 A | 10/1990 | Brautigam et al. | 204/182.3 |
| 5,151,165 A | 9/1992 | Huynh | 204/299 R |
| 5,284,559 A | 2/1994 | Lim et al. | 204/182.8 |
| 5,384,022 A | * 1/1995 | Rajasekaran | 204/616 |
| 5,776,767 A | 7/1998 | Stevens et al. | 435/287.2 |
| 5,871,628 A | 2/1999 | Dabiri et al. | 204/461 |
| 5,916,747 A | 6/1999 | Gilchrist et al. | 435/6 |
| 5,964,998 A | 10/1999 | Kambara | 204/452 |
| 5,991,030 A | 11/1999 | Yamamoto et al. | 356/346 |
| 5,993,634 A | 11/1999 | Simpson et al. | 204/612 |
| 6,004,446 A | 12/1999 | Middendorf et al. | 204/618 |
| 6,005,663 A | * 12/1999 | Waterhouse et al. | 356/344 |
| 6,014,213 A | 1/2000 | Waterhouse et al. | 356/344 |
| 6,017,434 A | 1/2000 | Simpson et al. | 204/612 |
| 6,017,765 A | 1/2000 | Yamada et al. | 436/47 |
| 6,056,859 A | * 5/2000 | Ramsey et al. | 204/451 |

OTHER PUBLICATIONS

"Automated DNA Fragment Collection by Capillary Array Gel Electrophoresis in Search if Differentially Expressed Genes," T. Irie et al., *Electrophoresis* 2000, 21, pp. 367–374.
"Preparative Electrophoresis in a Concentrated Polymer Solution: Automated Procedure for Microsome Isolation," Chang et al., *Analytical Biochemistry*, 1997, Article No. AB972048, pp. 111–114.
Japanese Patent No. 9–318600, "DNA Sequencer," published Dec. 12, 1997, Abstract only.
Japanese Patent No. 9–243597, "Multi–Capillary DNA Sequencer," published Sep. 19, 1997, Abstract only.
Japanese Patent No. 9–243562, "DNA Sequencer," published Sep. 19, 1997, Abstract only.
European Patent No. 0 735 365, "DNA base sequencer," published Oct. 2, 1996, Abstract only.
European Patent No. 0 724 153, "DNA Base sequencer," published Oct. 2, 1996, Abstract only.
European Patent No. 0 645 622, "DNA base sequencer," published Oct. 2, 1996, Abstract only.

* cited by examiner

Primary Examiner—Kaj K. Olsen
(74) Attorney, Agent, or Firm—Madson & Metcalf (57) ABSTRACT

An automatic sample collection system for use with an electrophoretic slab gel system is presented. The collection system can be used with a slab gel have one or more lanes. A detector is used to detect particle bands on the slab gel within a detection zone. Such detectors may use a laser to excite fluorescently labeled particles. The fluorescent light emitted from the excited particles is transmitted to low-level light detection electronics. Upon the detection of a particle of interest within the detection zone, a syringe pump is activated, sending a stream of buffer solution across the lane of the slab gel. The buffer solution collects the sample of interest and carries it through a collection port into a sample collection vial.

32 Claims, 4 Drawing Sheets

SAMPLE COLLECTION SYSTEM FOR GEL ELECTROPHORESIS

GOVERNMENTAL RIGHTS

This invention was made with Government support under Contract No. W-7405-ENG-36 awarded by the United States Department of Energy. The Government has certain rights in the invention.

BACKGROUND OF THE INVENTION

1. The Field of the Invention

The present invention relates to systems to separate and collect molecular samples. More specifically, the present invention relates to a system which automatically collects amino acid, protein and nucleic acid samples from gel electrophoresis.

2. Technical Background

Gel electrophoresis is a standard technique used for protein analysis, DNA fragment sizing, and DNA sequencing. Electrophoresis uses an electric field to cause differently charged particles in a sample to migrate at different rates. This difference in rate of migration results in the separation of the particles into bands of identical charge and size. Separation is based on charge and size difference between different molecules. Larger molecules migrate slower through a gel, while smaller molecules migrate more rapidly though a gel. Likewise, molecules which are highly charged migrate a at a faster rate than molecules with a lower charge.

A variety of gel electrophoresis devices are in use. A typical configuration of a device used for gel electrophoresis uses a flat slab of gel between two plates. The gel can be used in either a horizontal or a vertical position. Typically the slab gels have a thickness of about 0.5 mm to about 1.5 mm. The slab gels range from about 8 cm to about 50 cm high and from about 10 cm to about 20 cm wide. Some commercially available slab gel systems use pre-poured gel between disposable plates. Other systems use reusable plates into which a liquid gel is poured and then solidifies through polymer cross-linking or other mechanisms. In addition, pre-formed gels are also available.

Molecules such as proteins, polypeptides, and nucleic acids can be separated to form distinct bands on a slab gel. The particles are separated to a high resolution, meaning that particles with minute differences in charge and/or size are completely separated. A researcher may use gel electrophoresis to determine characteristics of an unknown sample such as size and charge of particles and the number of distinct fragments in the sample. Gel electrophoresis is also used to separate and purify a particular desired protein or nucleic acid from a mixture.

Gel electrophoresis is frequently used to determine the size of a DNA fragment. Nucleic acid molecules such as DNA have a relatively constant charge to size ratio which results in DNA molecules of the same size migrating uniformly in the gel. To determine the size of the DNA molecule of interest, a DNA ladder is mixed with the sample of interest and run on the gel. A DNA ladder consists of DNA fragments of known, but varying lengths. For example a 1,500 base pair (bp) DNA ladder has DNA segments ranging from 100 bp to 1,500 bp in 100 bp increments. The position of the unknown DNA fragment on the gel compared to the DNA ladder can be used to determine the size of the DNA fragment of interest. Prior to running the samples of DNA fragments or proteins on the gel slab, the samples are stained, radioactively labeled, or fluorescently labeled so that the position of the sample bands on the gel can be determined.

The same technique can be used to separate a DNA fragment of interest from a mixture of DNA fragments. Frequently, a researcher is looking for a DNA fragment or other nucleic acid of an approximate length. This desired DNA fragment is obtained in a sample mixed with other DNA fragments. The sample is then mixed with a DNA ladder and separated by gel electrophoresis. The researcher can determine which band on the gel is the desired DNA fragment by the position of the DNA ladder and the bands from the DNA sample. Once the DNA fragment of interest is identified, the band must be removed from the gel for further analysis and use. However, for the separated particle to be used for further analysis and manipulation, the sample bands must be recovered from the gel. Traditionally, removing the bands from the gel has been difficult. The methods used can be labor intensive. Moreover, the sample of interest can be contaminated or otherwise damaged.

Some methods for removing a sample of interest from a gel involve mechanically excising the portion of the gel containing the sample of interest. The sample of interest is then removed from the excised portion of the gel by either chemical or heat extraction methods. The purity of the sample obtained from these methods depend in large part on the skill of the person excising the sample from the gel. The sample of interest may also be denatured by the heat or chemicals used to remove it from the gel. Moreover, the processes take a long time and are not easily automated.

Other methods of manually extracting the sample of interest from the gel have been developed. These methods use electrophoresis to drive the particles into a membrane with a high affinity for DNA placed immediately downstream from the band of interest. The band is then removed from the membrane. Placement of the membrane in the gel can cause a disruption in the electrical field causing the particles to migrate around the membrane which can result in a low collection efficiency or a contaminated sample band.

These and other manual methods of obtaining the sample of interest from a slab gel have many defects. First, most of the methods are highly dependant on the skill of the operator. The methods are also labor intensive which makes the process more time consuming and costly. Moreover, the methods are not easily automated. Also, the methods can result in the contamination of the sample of interest. The heat and chemicals used in some of the methods may also damage the sample of interest.

Accordingly, a need exists for an apparatus that can automatically collect sample bands from a gel electrophoresis system. It would be an additional advancement if the apparatus, could cleanly extract the sample bands. It would be an additional advancement if the accuracy of the device were not dependant on the skill of the operator. It would be a further advancement if the system were capable of simultaneously extracting bands from multiple sample lanes. It would be a further advancement if the system did not use chemicals or temperatures which could damage the sample of interest. It would be an additional advancement if the device could extract a sample band from a slab gel without over diluting the sample. Such an apparatus is described and claimed herein.

BRIEF SUMMARY OF THE INVENTION

The apparatus of the present invention has been developed in response to the present state of the art, and in particular, in response to the problems and needs in the art that have not yet been fully solved by currently available systems and methods for collecting samples from slab gels. Thus, it is an overall objective of the present invention to provide an automatic collection system for collecting samples of interest from a gel electrophoresis slab gel.

To achieve the foregoing objects, and in accordance with the invention as embodied and broadly described herein in the preferred embodiments, an automatic sample collection system for gel electrophoresis is provided. The system is adaptable to be used with a slab gel with one or more lanes and may be retrofitted to existing slab gel systems. A sample of particles such as DNA, RNA, polypeptides, and proteins can be separated into sample bands on the slab gel. The sample collection system can automatically collect one or more of the sample bands. The sample bands can then be further purified and used by an operator of the sample collection system.

As the sample of particles is separated on the slab gel, the sample bands enter a detection zone. A detector is positioned to detect the entry of a particle within the detection zone. The detector can be used to scan all of the lanes of a multiple lane slab gel. Upon detection of the particle, a syringe pump is energized. The syringe pump directs a stream of buffer solution across a gel free zone within a lane of the slab gel. The buffer solution carries the sample band from the gel free zone, through a collection port, and into a collection vial. Generally the buffer solution used is the same buffer solution used in the slab gel. Accordingly, the buffer solution may contain tris-boric acid EDTA hereinafter, TBE, potassium tartrate, tris-acetate EDTA, hereinafter TAE, or other suitable buffers.

The detector of the present system can use a number of methods including UV-Vis absorbance, fluorescence, raman, mass spectrometry; and electrochemical detection. In a presently preferred embodiment, the detector uses fluorescence technology to detect the sample bands. Generally a fluorescent tag is attached to the particles of the sample. A laser can be positioned to excite the fluorescent tags on particles within the detection zone. The laser is selected to have a wavelength that excites the fluorescent tag. Thus when certain fluorescent dyes are used, an argon ion laser with a wavelength of about 488 nm is used.

An optical fiber can be imbedded in the gel to collect fluorescence from the excited particles. The optical fiber is positioned adjacent the sample lanes and within the collection zone. The fluorescence collected by the optical fiber is transmitted through the optical fiber to low-level light detection electronics such as photomultipliers, photodiodes, and CCD cameras. An optical filter may be positioned between the optical fiber and the low-level light detection electronics.

The collection system can be used to simultaneously collect samples from multiple lanes of a slab gel. The laser may be configured to be scanned between multiple lanes of the gel exciting any fluorescently labeled particles within a detection zone of any of the multiple lanes. Any flourescent light from the multiple lanes is transmitted by the optical fibers to low-level light detection electronics. The collection system can distinguish between fluorescence from the multiple lanes based on the position of the laser when the fluorescence is detected.

In another configuration, one or more optical fibers transmit the laser beam from the laser source to one or more detection zones. The one or more optical fibers allow one laser beam to be split and simultaneously be directed on multiple lanes of the slab gel. One or more additional detection optical fibers are positioned to collect any fluorescence from the labeled particles and transmit the light to low-level light detection electronics. An optical fiber switcher can be coupled to the detection optical fibers. The switcher allows the low-level light detection electronics to distinguish between the one or more lanes of the slab gel.

The present invention also relates to a method of collecting a sample band from gel electrophoresis. The method comprises obtaining a sample of interest and fluorescently labeling the sample. The sample is loaded into a gel electrophoresis system with an automatic sample collection system of the present invention. The gel electrophoresis system is activated to separate the particles of the sample of interest into sample bands. A sample band is detected by the sample collection system. A syringe pump is then activated to direct a stream of buffer across a lane of the slab gel. The stream of buffer collects the sample bands and carries the band into a collection vial.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the apparatus, system, and method of the present invention, as represented in FIGS. 1 through 4, is not intended to limit the scope of the invention, as claimed, but is merely representative of presently preferred embodiments of the invention.

Figure 1:
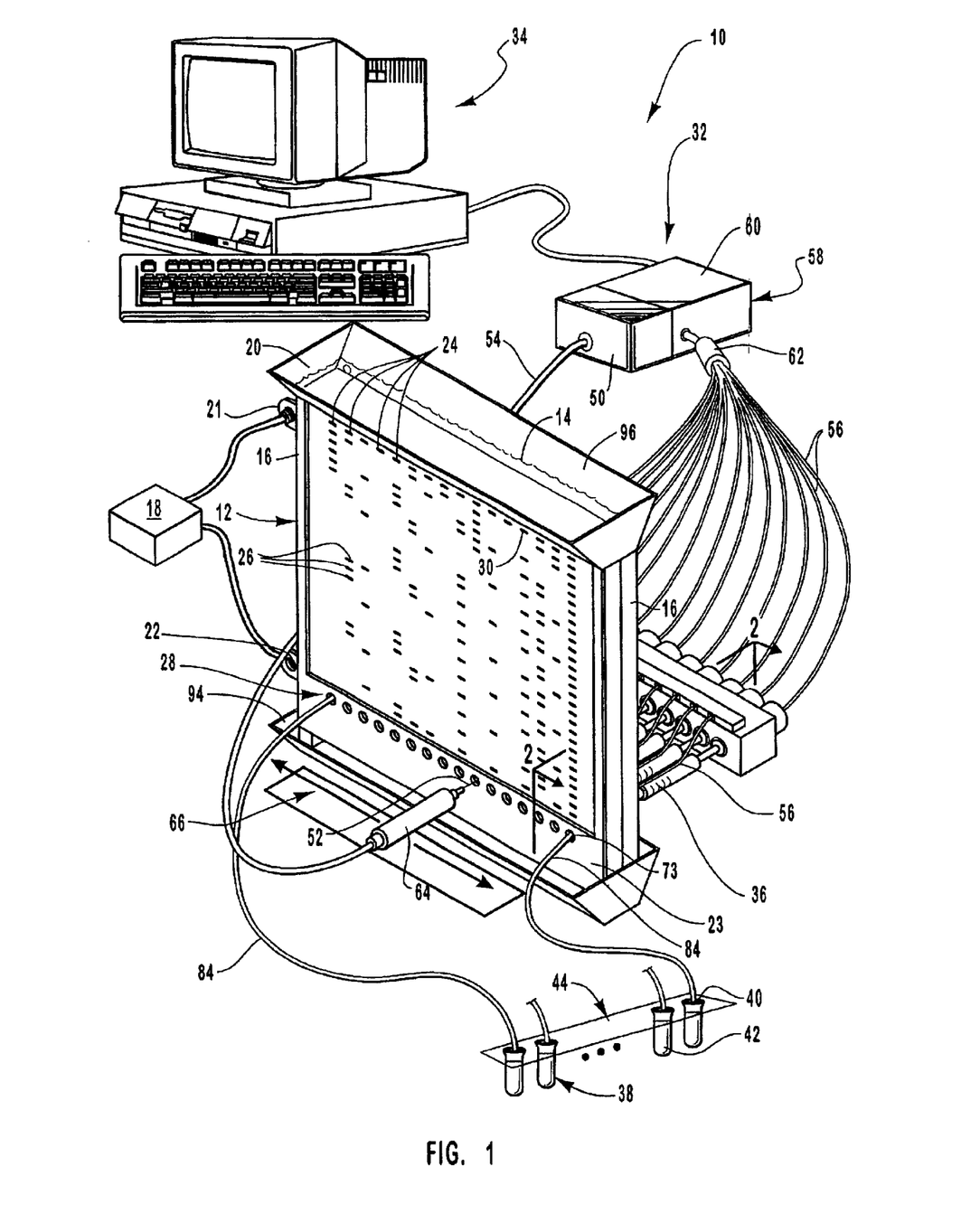
FIG. 1 is a perspective view of one embodiment of an automatic collection system.

Referring now to FIG. 1, an automatic collection system for use with a gel electrophoresis system is generally designated 10. The system can be used with a standard electrophoresis system 12. The automatic collection system 10 is depicted in conjunction with a vertical electrophoresis system 12, however, the collection system 10 can also be used with a horizontal electrophoresis system. The electrophoresis system 12 has a slab gel 14 positioned between two plates 16. The slab gel 14 is connected to an electrical source 18 which, when activated, applies a voltage across electrodes 21, 22. The voltage creates an electrical field within the slab gel 14.

A mixture of particles to be separated and collected is inserted into wells 24 positioned near the top 20 of the slab gel 14. Particles such as nucleic acids, polypeptides, and proteins are separated into distinct sample bands 26 as the particles migrate under the influence of the electrical field. Generally an electrolyte buffer solution is contained within the slab gel 14. The electrolyte buffer and gel allow a uniform electrical field to be established within the slab gel and assures that the particles uniformly migrate based on size and/or charge. Generally the electrolyte buffers used with standard electrophoresis systems 12 contain tris-boric acid EDTA hereinafter, TBE, and/or potassium tartrate, tris-acetate EDTA, hereinafter TAE, but are not limited to these. The gels can also be polyacrylamide, agarose, poly (ethylene oxide), and the like.

In certain configurations, the electrophoresis system 12 has two buffer reservoirs 94, 96 attached adjacent the top 20 and the bottom 23 of the slab gel 14. The buffer reservoirs 94, 96 can serve as the attachment point for the electrodes 21, 22. After the particles are inserted into the well, the buffer reservoirs 94, 96 are filled with an electrolyte buffer solution. This configuration allows a uniform electrical field to be established within the slab gel 14.

Under the uniform electric field, the particles migrate in a straight line toward the bottom 23 of the slab gel 14. The straight line of migration define a lane 30 within the slab gel 14. A slab gel 14 used with the automatic detection system 10 can have one or more lanes 30. A typical slab gel 14 used in electrophoresis has eight or sixteen lanes 30. However, the automatic collection system can be used with a gel having as few as one lane 30 or a slab gel 14 with substantially more than sixteen lanes 30.

A detection zone 28, is established within the slab gel 30. The detection zone 28 can be at almost any position along a lane 30 of the slab gel 14, provided that adequate distance is allowed in the lane 30 for the particles separate into definite, isolated sample bands 26. Generally, positioning the detection zone 28 toward the bottom 23 of the gel 14 provides a lane 30 with adequate separation distance. In a presently preferred configuration, the detection zone 28 is positioned about two inches from the bottom of the slab gel 14. This distance allows both for separation of the particle bands and prevents faster migrating particles from interfering with the collection of a sample band of interest.

A detector 32 monitors the detection zone 28 for the presence of a sample band 26 within the zone 28. When a sample band 26 is detected within the zone 28, the detector 32 signals a computer 34. The computer 34 tracks the migration of the sample bands 26 through the detection zone 28. When a sample of interest is detected, the computer 34 activates a syringe pump 36 which sends a stream of buffer solution across the lane 30 of the slab gel 14. The stream of buffer solution carries the sample band of interest from the slab gel into a collection vial 38.

The sample collection system 10 can be used to collect multiple bands from a single lane 30. For example if a sample contains twenty different particles, a user may wish to collect bands 2 and 7. The detector 32 will signal the computer 34 when band 1 passes, but will not activate the syringe pump 36. Upon the detection of band 2, the syringe pump 36 will be activated and band two collected in a first sample vial 40. Bands 3 through 6 will pass though the detection zone 28 without activation of the syringe pump 36. But when band 7 is detected, the computer 34 will activate the syringe pump again sending sample band 7 to a second collection vial 42. A fraction collector 44 can hold the multiple collection vials 38 and position a new vial 38 to be filled after each vial 38 is used.

The automatic sample collection system 10 can be configured to simultaneously scan and collect samples from multiple lanes 30. A single detector 32 can be configured to scan multiple lanes 30 for the presence of a sample band 26 within the lanes 30. When a desired band 26 is detected within any of the lanes, the computer 34 signals one of an array of syringe pumps 36 to activate. The computer 34 activates the syringe pump 36 corresponding to the lane 30 wherein the sample band of interest is contained. The activated syringe pump 36 forces a stream of buffer across the lane 30. The sample band 26 of interest is collected in a sample vial 38. An array of fraction collectors 44 can be used with a fraction collector 44 corresponding to each of the lanes 30 of the slab gel 14. Thus, the automatic collector 10 can simultaneously collect multiple sample bands 26 from multiple lanes 30.

The detector 32 can use a variety of detection methods such as raman and radiolabeling to detect the presence of a sample band 26 within the detection zone 28. In the illustrated embodiment, fluorescence technology is used for detection of the bands 26. Fluorescent technology uses a fluorescent dye including, but not limited to cyanine nucleic acid dyes, a range of which are commercially available from Molecular Probes, Inc., Eugene, Oreg. Specific examples of useful fluorescent dyes are sold under the trademarks PicoGreen®, TO-PRO 1, and TO-PRO 3. The fluorescent dye is attached to the sample of interest. The fluorescent tags emit light when excited by a laser of a certain wavelength. The light from the excited fluorescent tag is known as laser induced fluorescence.

The laser which is selected to excite the fluorescent tag depends on the tag itself. For example, TO-PRO-3 intercalating dye (642/661 nm Ex/Em) can be easily excited with a small HeNe laser at 635 nm. Using TO-PRO-3 allows the system to be quite sensitive, however, the sensitivity of the system can be improved dramatically by using other dyes such as PicoGreen (498/520 nm Ex/Em). PicoGreen can be excited with an argon ion laser at 488 nm. Using diode lasers at 500 nm can allow for fluorescent detection of the sample bands 26 while using a smaller laser.

In the illustrated embodiment, the sample of particles is labeled with a fluorescent tag. A laser 50 directs a laser beam 52 into an optical fiber 54 coupled to the laser 50. The optical fiber 54 transmits the laser beam 52 to the detection zone 28. A labeled band 26 within the detection zone 28 will fluoresce under the laser beam. The fluorescent light from the band 26 is collected within a collection optical fiber 56 embedded in the gel 14. The fluorescent light is transmitted by the optical fiber 56 to a light detector 58.

The light detector 58 can be low-level light detection electronics 60 such as photomultipliers, photodiodes or CCD cameras. An optical filter 62 is positioned between the fiberoptic 56 and the light detection electronics 60 to prevent incident light from the laser beam 52 from reaching the detection electronics 60. The filter 62 is selected such that it maximizes detection of the fluorescent light while minimizing or rejecting the background light from the excitation beam hitting the detector. The optical filter 62 can be a combination of a high band pass filter 62, for example greater than about 500 nm, with a notch filter 62 at the wavelength of the laser beam 52 for example about 488 nm. Alternatively, the filter 62 may be a narrow band pass filter 62 at the emission wave length corresponding the fluorescence of the fluorescent tags. For example a narrow band pass filter 62 in the range of about 520 nm plus or minus about 10 nm has been used. Other methods of filtering light such as a prism may be also used.

The laser beam 52 is focused on the detection zone 28 to achieve the maximum light intensity without causing the fluorescent tags to photo-bleach. The focusing of the beam 52 also minimizes the width of the laser beam 52. Because the minimized beam 52 directs light onto only a very small portion of the slab gel 16 at a given time, the system 10 can detect a small separation distance thereby maximizing the detection efficiency of the system 10.

The power of the laser beam 52 can be optimized to provide maximum fluorescing of the fluorescent tags while minimizing the background light transmitted to the light detection electronics 60. A laser beam 52 with a power in the range from about 1 mW to about 100 mW allows for sufficient fluorescing of the tags while minimizing the interfering background. In a presently preferred embodiment of the system 10, the excitation beam has a power of about 30 mW.

Figure 2:
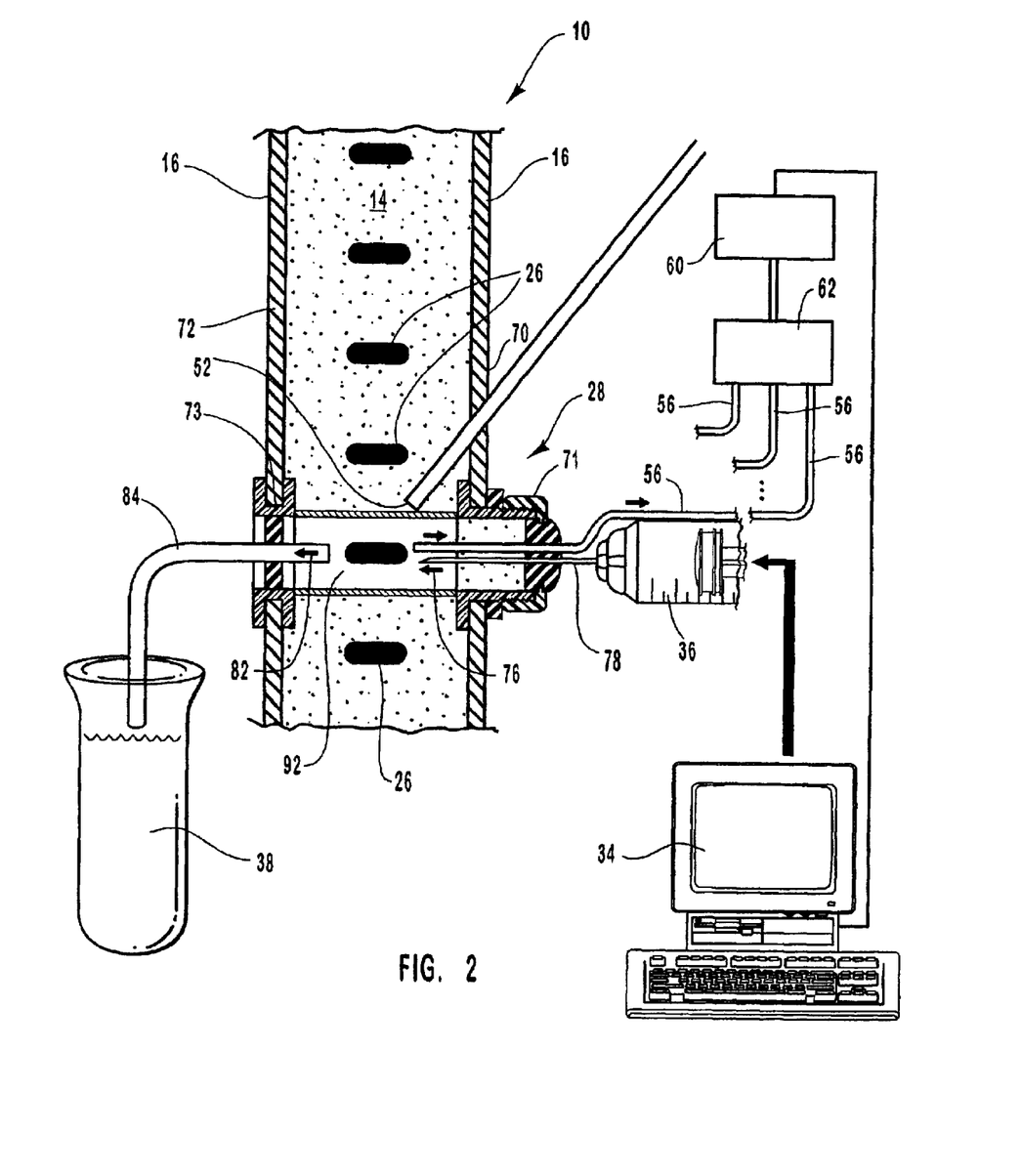
FIG. 2 is an expanded cross sectional view of the embodiment of FIG. 1 taken across lines 2—2.

The optical fiber 54 is attached to a motorized X-Y stage 66 controlled by the computer 34. The stage can move the fiberoptic head 64 of the optical fiber 54 to precisely position the laser beam 52 in any of the detection zones 28. The motorized stage 66 can move the position of the optical fiber head 64 back and forth across the slab gel 14 to direct a single laser beam 52 on all of the lanes. In this manner the laser 50 can be used to detect sample bands 26 in all lanes 30 of the system 10. Referring now to FIG. 2, a cross sectional view of a lane of the slab gel 14 is shown within the detection zone 28. The slab gel 14 is bordered by a front plate 70 and a back plate 72. Each of the plates are fitted with a manifold 71, 73. The manifold 71, 73 allow access through the plates 70, 72 to the slab gel 14. Generally the plates 70, 72 are made of glass. However, when the manifolds 71, 73 are formed by drilling holes into the plates 70, 72, it may be difficult to drill very small holes. In one embodiment the plates 70, 72 are made of polycarbonate. The polycarbonate plates 70, 72 are mechanically or chemically roughened to prevent the gel 14 from migrating with the electric field. Generally the manifolds 71, 73 have an inside diameter in the range from about 1/64 inch to about 1/8 inch.

At the time of casting of the gel 14 between the plates 70, 72 a solid rod plug is inserted into manifolds 71, 73. The plug is removed once the gel solidifies, leaving a gel free zone 92. This zone 92 allows electronmigration of analyte bands 26 while creating a low pressure region for buffer liquid to flow from syringe 36, through the zone 92. The flowing buffer collects an analyte bands 26, into the tube 84, and vial 38. Once the plug is removed, an electrolyte buffer solution is injected into the gel free zone to allow the electrical field to remain undisturbed within the gel free zone 92. As a practical matter the gel free zone 92 is aligned with the detection zone 28 allowing the bands 26 to be detected and collected, generally simultaneously.

In a first manifold 71 a collection optical fiber 56 collects fluorescent light as the laser beam 52 excites the sample band 26. The collection optical fiber 52 transmits the light to the light detection electronics 60 which then signals the computer to activate the syringe pump. The activated syringe pump 36 then sends a stream of buffer though a first capillary 78 though the gel free zone 92 and into a collection port 82 within the second manifold 73. The stream of buffer 76 carries the sample band from the gel free zone 92 into the collection port 82. From the collection port 82, the stream of buffer travels though a second capillary 84 into a sample collection vial 38.

Figure 3:
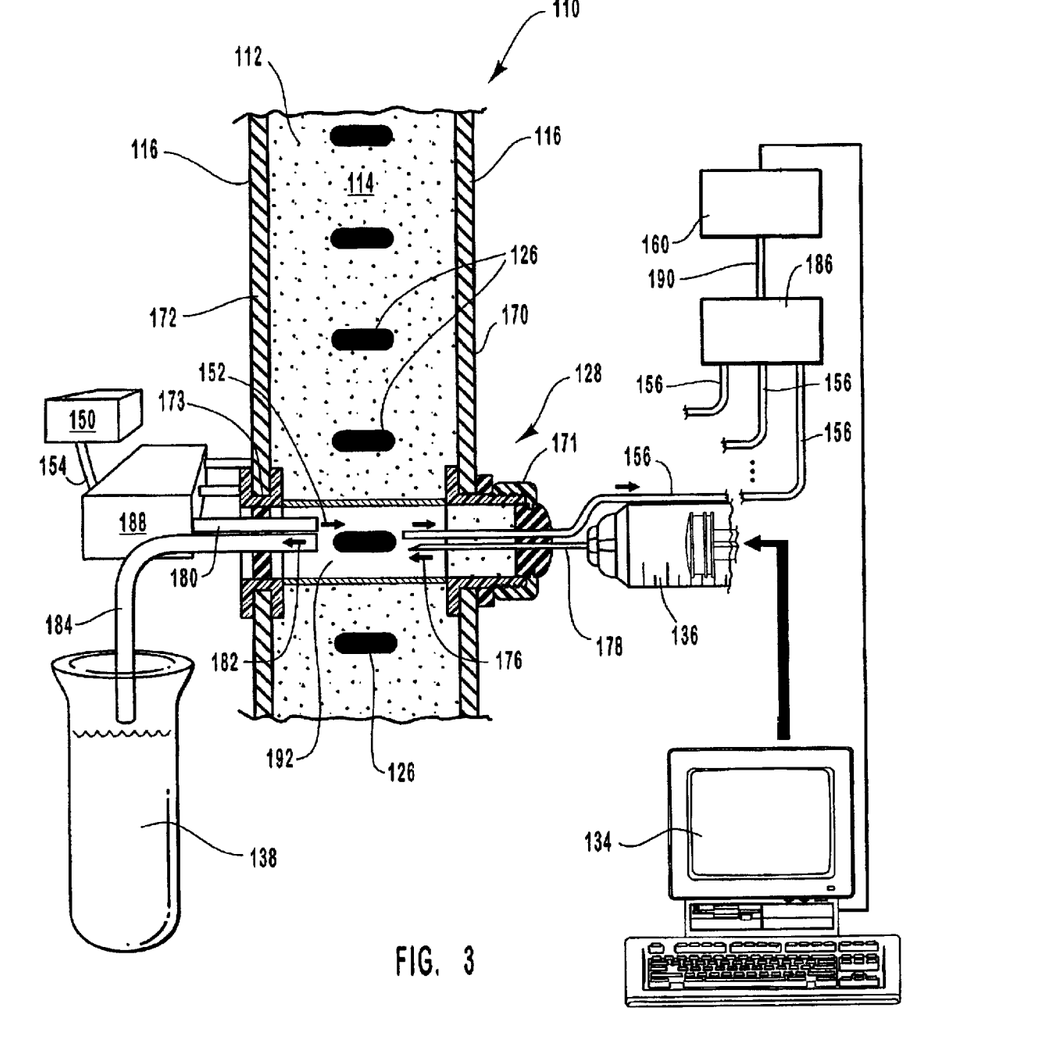
FIG. 3 is an expanded cross section view of an alternative embodiment of the invention.

Referring now to FIG. 3, an alternative embodiment of automatic collection system of the present invention is generally designated 110. The collection system 110 is shown with a cross section taken through one of the detection zones 128. The system 110 uses the same general components and parameters as the system 10. However, the laser beam 152 is not rastered between the detection zones 128 in the system 110. In the embodiments of FIG. 3, a fiber optic 154 is coupled to the laser 150. The fiber optic 154 transmits the laser light 152, to a beam splitter 188 which divides the laser beam 152 into multiple laser beams 152. The beam splitter 188 transmits the split beams 152 to a series of transmission optical fibers 180. Each of the multiple transmission optical fibers 180 directs the laser beam 152 into a detection zone 128 of a separate lane 130 of the slab gel 114.

The system 110 has a first manifold 171 and a second manifold 173. The transmission optical fiber 180 enters the detection zone 128 thought the second manifold 173. The laser beam 152 exits the transmission optical fiber 180 and excites a sample band 126 within the detection zone. A light collection optical fiber 156 enters the detection zone 128 through the first manifold 171 and collects fluorescent light as the laser beam 152 excites the sample band 26. The collection optical fiber 156 transmits the light to an optical fiber switcher 186. From the optical fiber switcher 186, the fluorescent light is transmitted through another optical fiber 190 to the light detection electronics 160 which then signal the computer 134 to activate the syringe pump 136. The activated syringe pump 136, then sends a stream of buffer though a first capillary 178 though the gel free zone 192 and into a collection port 182. The stream of buffer 176 carries the sample band from the gel free zone 192 into the collection port 182. From the collection port 182, the stream of buffer travels though a second capillary 184 into a sample collection vial 138.

When multiple lanes 130 are being monitored, multiple transmission optical fibers 156 can transmit fluorescent light to the optical fiber switcher 186 at the same time. The computer 134 uses the switcher 186 to change between the optical fibers 156 so that light from only one lane 116 at a time is sent to the light detection electronics 160. In this manner the computer 134 distinguishes between the signal from the multiple lanes 130 and activates the syringe pump 136 corresponding to the correct lane 130.

EXAMPLES

The following examples are given to illustrate various embodiments which have been made with the present invention. It is to be understood that the following examples are not comprehensive or exhaustive of the many types of embodiments which can be prepared in accordance with the present invention.

Example 1—Fluorescence Detection Across Multiple Lanes

Figure 4:
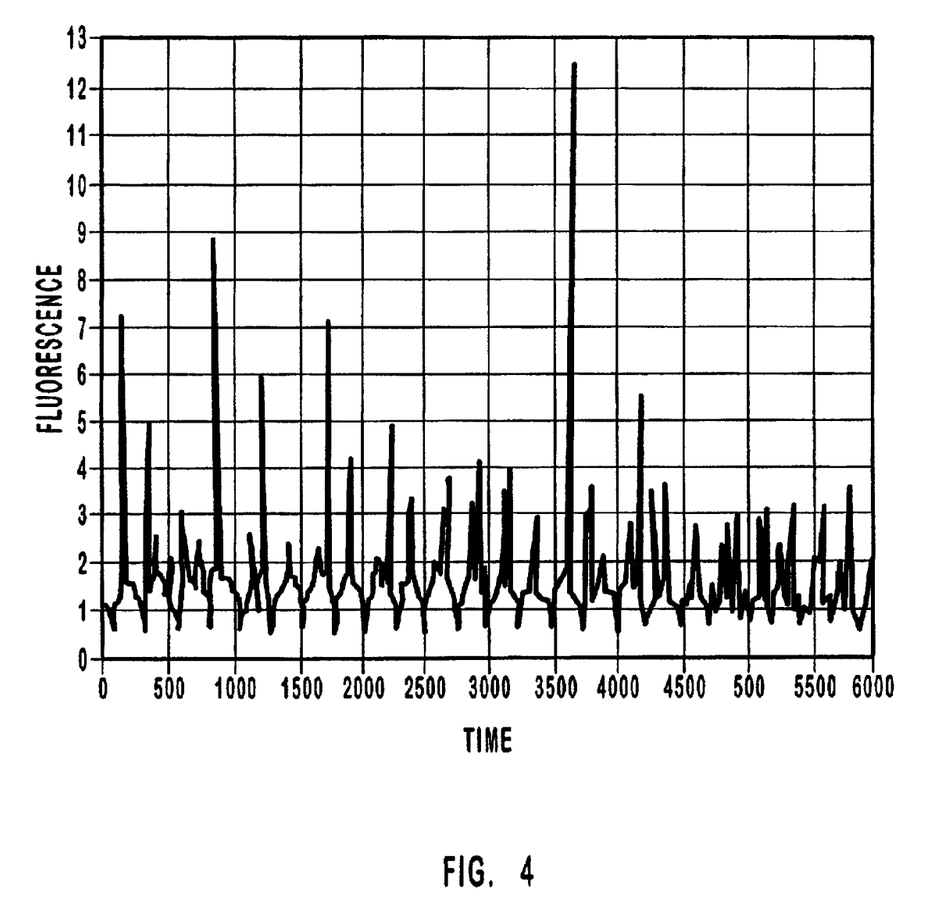
FIG. 4 is a graph illustrating laser induced fluorescence detection across multiple lanes of a slab gel by a single laser.

An electrophoresis slab gel was used to separate a DNA sample. The gel is acrlyamide buffer gel with TBE. The DNA sample was labeled with a fluorescent dye. About 3 kV was applied to the slab gel for about 24 hours. A 488 nm laser with an optical fiber head was scanned across the eight lanes of the gel using a motorized X-Y table. Fluorescence was detected by a reflectance probe positioned within the gel. The reflectance probe had an optical fiber head which collected any light from the fluorescing particles and transmitted the light to a photomultiplier tube. As shown in the electropherogram of FIG. 4, the fluorescently labeled DNA sample bands were detected in all lanes of the slab gel.

SUMMARY

In summary, an automatic sample collection system for use with an electrophoresis system is presented. A detector is provided to detect the presence of a sample band within a detection zone. When a desired sample band is detected a syringe pump containing a buffer solution is energized and directs a buffer solution across a lane of a slab gel. The buffer solution can be the same buffer solution as that used in the slab gel. The buffer solution collects the sample band and transports it to a collection vial. The system can use fluorescence detection to detect the particle bands. A system is provided capable of collecting multiple sample bands from multiple lanes of the slab gel. The entire collection process can be automated and controlled by a computer.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed and desired to be secured by United States Letters Patent is:

1. An automatic sample collection device for use with a slab gel electrophoresis system having one or more lanes, the sample collection system comprising:
    a detection zone within the slab gel;
    a detector for detecting a sample of interest within the detection zone;
    a gel free zone within the slab gel, wherein the gel free zone is filled with a buffer solution, wherein the detection zone and the gel free zone are aligned with each other; and
    a collector for collecting the detected sample of interest comprising an energizable pump operably connected to the detector, the energizable pump configured to direct a low volume stream of liquid buffer solution onto a detected sample of interest, thereby collecting the sample of interest within the stream of buffer solution.

2. The automatic sample collection device of claim 1, wherein the collector further comprises a sample collection vial configured to receive the stream of liquid buffer solution and the collected sample of interest.

3. The automatic sample collection device of claim 1, wherein the buffer solution is selected from the group consisting of TAE (tris-acetate EDTA), potassium tartrate, and TBE (tris-boric acid EDTA).

4. The automatic sample collection device of claim 1, wherein the detector comprises a fluorescent tag attachable to a sample of interest.

5. The automatic sample collection device of claim 4, wherein the detector further comprises a laser positioned to direct a laser beam to excite the fluorescent tag within the detection zone.

6. The automatic sample collection device of claim 5, wherein the laser beam is scanned between multiple lanes of the slab gel.

7. The automatic sample collection device of claim 5, further comprising one or more transmission optical fibers connecting the laser with one or more detection zones of a slab gel, the one or more transmission optical fibers configured to transmit a laser beam from the laser to one or more detection zones.

8. The automatic sample collection device of claim 5, wherein the laser is an argon ion laser.

9. The automatic sample collection device of claim 5, wherein the detector further comprises one or more collection optical fiber imbedded within the gel.

10. The automatic sample collection device of claim 9, wherein the one or more collection optical fibers are positioned adjacent one of the one or more sample lanes and to collect light emitted from the fluorescent tag.

11. The automatic sample collection device of claim 5, wherein the detector further comprises low-level light detection electronics.

12. The automatic sample collection device of claim 11, wherein the low-level light detection electronics are selected from the group comprising photomultipliers, photodiodes and CCD (charge coupled device) cameras.

13. The automatic sample collection device of claim 11, wherein the detector further comprises an optical filter positioned between a collection optical fiber imbedded within the gel and the low-level light detection electronics.

14. The automatic sample collection device of claim 13, wherein the optical filter comprises a high band pass filter for filtering light with a wavelength greater than about 500 nm and a notch filter.

15. The automatic sample collection device of claim 14, wherein the optical filter comprises a narrow band pass filter which filters light other than light with a wavelength corresponding to the wavelength of the light emitted from the fluorescent label, ±10 nm.

16. The automatic sample collection device of claim 1, wherein the sample of interest is selected from the group comprising a nucleic acid, a polypeptide, and a protein.

17. A sample collection system for use with an electrophoretic slab gel having one or more sample lanes, the sample collection system comprising:
    a detection zone within the slab gel;
    a fluorescent tag attachable to a sample of interest,
    a laser configured to direct a laser beam on the fluorescent tag when the sample of interest is within the detection zone, the laser beam exciting the fluorescent tag;
    low-level light detection electronics positioned to detect light from the excited fluorescent tag;
    a gel free zone within the slab gel, wherein the gel free zone is filled with a buffer solution, wherein the detection zone and the gel free zone are aligned with each other; and
    a collector for collecting the detected sample of interest, wherein the collector comprises an energizable pump operably connected to the low level light detection electronics, the energizable pump configured to direct a stream of liquid buffer solution onto a sample of interest within a gel free zone, thereby collecting the sample of interest within the stream of buffer solution.

18. The sample collection system of claim 17, wherein the collector further comprises a sample collection vial configured to receive the stream of liquid buffer solution and the collected sample of interest.

19. The sample collection system of claim 17, wherein the laser is an argon ion laser.

20. The sample collection system of claim 17, wherein the fluorescent tag is a cyanine nucleic acid dye.

21. The sample collection system of claim 17, further comprising a collection optical fiber imbedded within the slab gel and positioned to collect fluoresce from the excited fluorescent tag.

22. The sample collection system of claim 21, further comprising an optical filter positioned between the optical fiber and the low-level light detection electronics.

23. The sample collection system of claim 21, wherein the optical fiber is positioned adjacent one of the one or more sample lanes and to collect light emitted from the fluorescent tag.

24. The sample collection system of claim 17, wherein the low-level light detection electronics are selected from the group comprising photomultipliers, photodiodes and CCD (charge coupled device) cameras.

25. The sample collection system of claim 17, wherein the sample of interest is selected from the group comprising a nucleic acid, a polypeptide, and a protein.

26. A method of collecting a sample band from a electrophoresis slab gel, the method comprising:

obtaining a sample of interest;

loading the sample of interest into a lane of a gel electrophoresis system with one or more sample lanes, the gel electrophoresis system comprising a sample collection system comprising a detection zone within the slab gel, a detector for detecting a sample of interest within the detection zone, a gel free zone within the slab gel, wherein the gel free zone is filled with a buffer solution, wherein the detection zone and the gel free zone are aligned with each other, and a collector for collecting the detected sample of interest, wherein the collector comprises an energizable pump operably connected to the detector, the energizable pump configured to direct a stream of liquid buffer solution onto a detected sample of interest within a gel free zone, thereby collecting the sample of interest within the stream of buffer solution;

detecting a sample within the detection zone; and collecting the sample of interest from the slab gel.

27. The method of claim 26, further comprising energizing the pump.

28. The method of claim 26, wherein the sample of interest is selected from the group comprising a nucleic acid, a polypeptide, and a protein.

29. The method of claim 26, wherein the detector comprises a fluorescent tag attachable to a sample of interest.

30. The method of claim 26, wherein the detector comprises a laser positioned direct a laser beam on the fluorescent tag, the laser beam exciting the fluorescent tag within the detection zone, the method further comprising activating the laser to excite the fluorescent tag.

31. The method of claim 26, wherein the detector further comprises low-level light detection electronics.

32. The method of claim 31, wherein the low-level light detection electronics are selected from the group comprising photomultipliers, photodiodes and CCD (charge coupled device) cameras.

* * * * *